United States Patent [19]

Moenkhaus

[11] Patent Number: 4,561,288
[45] Date of Patent: Dec. 31, 1985

[54] FLUE GAS ANALYZER WITH CARBON MONOXIDE DETECTOR

[75] Inventor: Patrick R. Moenkhaus, Moundsview, Minn.

[73] Assignee: Honeywell Inc., Minneapolis, Minn.

[21] Appl. No.: 608,758

[22] Filed: May 10, 1984

[51] Int. Cl.[4] ............................................. G01N 31/00
[52] U.S. Cl. ................................... 73/23; 73/863.61; 73/863.83; 73/863.86
[58] Field of Search ................. 73/23, 863.31, 863.61, 73/863.83, 863.86, 864.34

[56] References Cited

U.S. PATENT DOCUMENTS

| | | | |
|---|---|---|---|
| 3,759,087 | 9/1973 | Iwao et al. | 73/23 |
| 3,960,500 | 6/1976 | Ross et al. | 73/23 |
| 4,030,887 | 6/1977 | Poli et al. | 73/23 |
| 4,165,630 | 8/1979 | Felder et al. | 73/23 |
| 4,251,225 | 2/1981 | Hanada et al. | 73/23 |
| 4,485,666 | 12/1984 | Higgius et al. | 73/23 |

FOREIGN PATENT DOCUMENTS 524839 10/1976 U.S.S.R. .................. 73/23

OTHER PUBLICATIONS

Installation and Instruction Sheet, Form 60-2543, of the A7001 Combustion Efficiency Analyzer, (Honeywell Inc.).

Primary Examiner—David L. Lacey
Attorney, Agent, or Firm—Alfred N. Feldman

[57] ABSTRACT

A flue gas analyzer connects a carbon monoxide gas analyzer cell into a flue gas system to analyze accurately the carbon monoxide content of a flue gas sample. A predetermined flow of flue gas through the analyzer cell at a constant rate is provided by a pump and orifice configuration to accurately determine the carbon monoxide content of the flue gas.

11 Claims, 2 Drawing Figures

FLUE GAS ANALYZER WITH CARBON MONOXIDE DETECTOR

BACKGROUND OF THE INVENTION

The operation of burners used in industrial, commercial, residential furnaces, heat treating ovens, and boilers is well recognized. The desire to operate these burners as efficiently as possible has become essential due to the escalating cost of fuel. Many different techniques and pieces of equipment are used to obtain the most efficient type of burner operation.

The chemistry of combustion is well established with mathematical formulas that accurately describe all phases of the process. In its simplest form, combustion is the combination of oxygen from the air with hydrogen and carbon from the fuel to form carbon dioxide, water, and energy (in the form of light and heat).

Perfect combustion occurs when all of the carbon and hydrogen in the fuel unites with all of the oxygen supplied by the air. For this to happen, three factors must occur. These three factors are that the temperature is high enough for the fuel/air mixture to ignite. That sufficient turbulence of the fuel and air are present to provide the necessary mixing. And, that sufficient time is allowed for the fuel and oxygen to burn. In the real world, perfect combustion is extremely difficult to achieve and the usual fuel/air ratio will not completely burn. Therefore, a controlled amount of extra or excess air is added, increasing the chance that all of the fuel will mix with oxygen in time to burn completely and minimize incomplete combustion. Incomplete combustion is costly because it produces partially burnt fuels in the form of smoke and carbon monoxide. These products escape up the flue carrying away large amounts of otherwise usable energy.

Too much excess air wastes energy also. First, energy is lost heating the incoming excess air. Second, the excess air increases the volume of heated gasses passing through the boiler. The heated gasses spend less time in the boiler and as a result transfer less energy from the combustion gases to the boiler fluid.

In an effort to minimize these losses, it has been beneficial to utilize various types of combustion analyzers. One analyzer is an A7001 Combustion Efficiency Analyzer as sold by Honeywell. The A7001 Combustion Efficiency Analyzer is used by burner service technicians to sample and analyze flue gas from various types of burners. The parameters measured include: percent of oxygen concentration in the flue gas, flue gas temperature rise, and smoke spot number. The meter also displays combustion efficiency based on flue gas oxygen content, temperature rise, and fuel properties. Service technicians use this information when adjusting burner fuel to air ratios to achieve an optimum combustion efficiency.

In certain types of applications it is also necessary to measure and adjust the optimum operation with the carbon monoxide content as one of the parameters. This is accomplished by extracting a sample of the flue gas as it passes up the stack. The sample is then chemically analyzed. The analysis can be manual or can be accomplished by extracting a carefully controlled amount of flue gas through a chemical cell. The extraction is accomplished by a hand-operated type of draw pump, and is subject to many variations due to the mode of operation of the pump.

SUMMARY OF THE INVENTION

The present invention is directed to the utilization of a gas detector tube or carbon monoxide gas analyzer cell that has been used to analyze flue gases for carbon monoxide content in hand-held units. The gas indicator tube or cell requires that a one hundred milliliter sample of flue gas be drawn through the tube, and that the sample be drawn in a very uniform and consistent manner. A chemical along the length of the tube is progressively discolored by the flue gas sample with the discoloration progressing more or less within the tube according to the concentration of carbon monoxide in the flue gas. The final location of the leading edge of a stain in the cell indicates the carbon monoxide content, typically in parts per million, and is read directly on a scale which is printed on the surface of the tube.

The discoloration or stain is the result of a chemical reaction, the reduction by carbon monoxide of potassium palladosulfite to liberate metallic palladium. This reaction proceeds at a rate determined, in part, by the flow rate of the gas through the tube. To ensure maximum accuracy, therefore, it is important to maintain a constant flow rate through a predetermined sensing interval.

The present invention utilizes an electrically driven pump that is operated for a timed interval to draw a constant flow rate through the chemical sensing tube. The operation of the chemical sensing tube or carbon monoxide gas analyzer cell means is accomplished, therefore, in a uniform and precise manner. This allows for accurate measurement of the carbon monoxide sample being drawn from a stack. The utilization of a pump and timing circuit of a device such as the A7001 Combustion Efficiency Analyzer simplifies and ensures the accuracy of the measurement of carbon monoxide when using carbon monoxide gas analyzer cell means of the type disclosed.

In accordance with the present invention, there is provided a flue gas analyzer means including a probe adapted to be inserted in a flue gas stack to withdraw a flue gas sample for analysis, including: flue gas analyzer means having probe housing means and console means electrically connected to form said analyzer means with said housing means including fitting means for attachment of said probe to said housing means; said housing means including pump means to draw said flue gas through said probe, said fitting means, and an analyzer portion of said flue gas analyzer means; said flue gas analyzer means also including timer means connected to said pump means to time the operation of said pump means to draw a predetermined volume of flue gas from said stack through said probe and said fitting means; and said fitting means including carbon monoxide gas analyzer cell means with said flue gas analyzer means providing for a predetermined flow of said flue gas through said carbon monoxide gas analyzer cell means at a constant rate to accurately determine the carbon monoxide content of said flue gas.

DESCRIPTION OF THE PREFERRED EMBODIMENT

Figure 1:
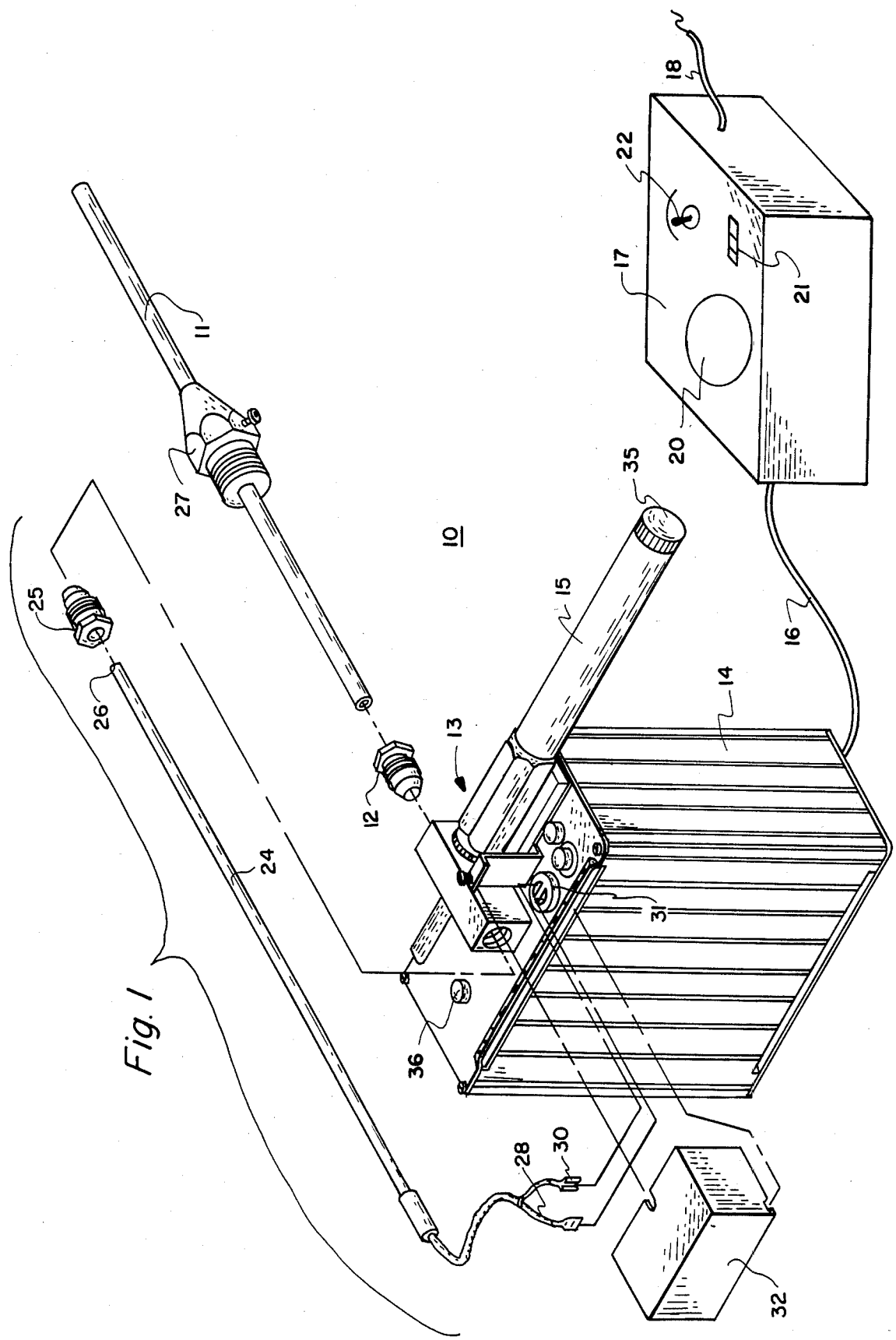
FIG. 1 is an isometric view of a flue gas analyzer including a carbon monoxide gas analyzer cell means.

In FIG. 1 there is disclosed an isometric view of a flue gas analyzer means 10 that is capable of also measuring the carbon monoxide content of a flue stack gas. The flue gas analyzer means 10 includes a probe 11 that is connected by a ferrule 12 into a fitting means 13 that forms part of a probe housing means 14. The fitting means 13 includes a cylindrical housing means 15 that includes a carbon monoxide measuring cell and which will be described in detail in connection with FIG. 2.

The probe housing means 14 is connected by cable 16 to a console 17 that is shown energized from a conventional line source 18. The console 17 includes a meter 20, a mode selection switch 21, and a rotary switch 22 for selection of the function to be read out by the meter 20. The flue gas analyzer means 10 is completed by the addition of a thermocouple 24 that fits through a ferrule 25 into the fitting means 13 so that an end 26 of the thermocouple 24 fits into the probe 11 at a point approximating where the probe 11 is exposed to the flue gas in a stack. The probe 11 can be conveniently positioned by a conical fitting 27. The thermocouple 24 has a pair of leads 28 and 30 that are plugged into a plug 31 that forms part of the probe housing means 14. The plug 31 and its associated wiring are conveniently covered by a protective cover 32 to complete the device.

It will be understood that the probe housing means includes a pump means and an analyzer portion of an oxygen sensing type of cell. The pump means draws flue gas through the probe 11 into the fitting means 13 where it is drawn into the probe housing means 14. A zirconium oxide type of oxygen sensor measures the oxygen content in the flue gas. At the same time, the thermocouple 24 provides a signal on the conductors 28 and 30 to the plug 31 to supply the probe housing means 14 with information on the temperature at the point where the flue gas is sampled. The probe housing means 14 contains further electronics and circuitry that are interconnected by the cable 16 to the console 17. The console 17 contains various electronic circuits that analyze the information from the thermocouple and the zirconium oxide sensor to provide a reading on meter 20 of such items as the oxygen reading, the flue gas temperature rise, and efficiency reading. A smoke spot measurement is possible with this equipment also, but has not been specifically described. The flue gas, after it has been sampled, is vented to the atmosphere through vent opening 36 and is of relatively small quantity compared to the surrounding atmosphere so that it does not constitute a hazard.

The device of FIG. 1 includes the capability of also measuring the carbon monoxide in the flue gas being samples by the probe 11. This is accomplished by drawing a flue gas sample through the probe 11 and into the fitting means 13. The sample is drawn by the pump within the probe housing means 14 into the cylindrical housing means 15. The cylindrical housing means 15 contains a carbon monoxide gas analyzer means or chemical cell that measures the carbon monoxide content as was previously described. The housing means 15 will be described in detail in connection with FIG. 2. It should be understood that the flue gas drawn through the probe 11 and into the fitting means 13 is circulated through the center of the cylindrical housing means 15 to an end 35. At the end 35 a reentrant flow path (which will be shown in detail in FIG. 2) exists and the flue gas is drawn back through the cylindrical housing means 15 into the fitting means 13 and fed back to the venting system so that all of the flue gas is vented from the opening 36 in the probe housing means 14. The opening 36 could be located at any convenient point.

After a timed operating cycle of the pump means contained within the probe housing means 14, a controlled sample of flue gas has been drawn through the analyzer cell means that is contained in the cylindrical housing means 15. The cylindrical housing means 15 is then removed and a scale on the side of the cell means is read to determine the carbon monoxide content of the flue gas extracted by the probe 11.

Figure 2:
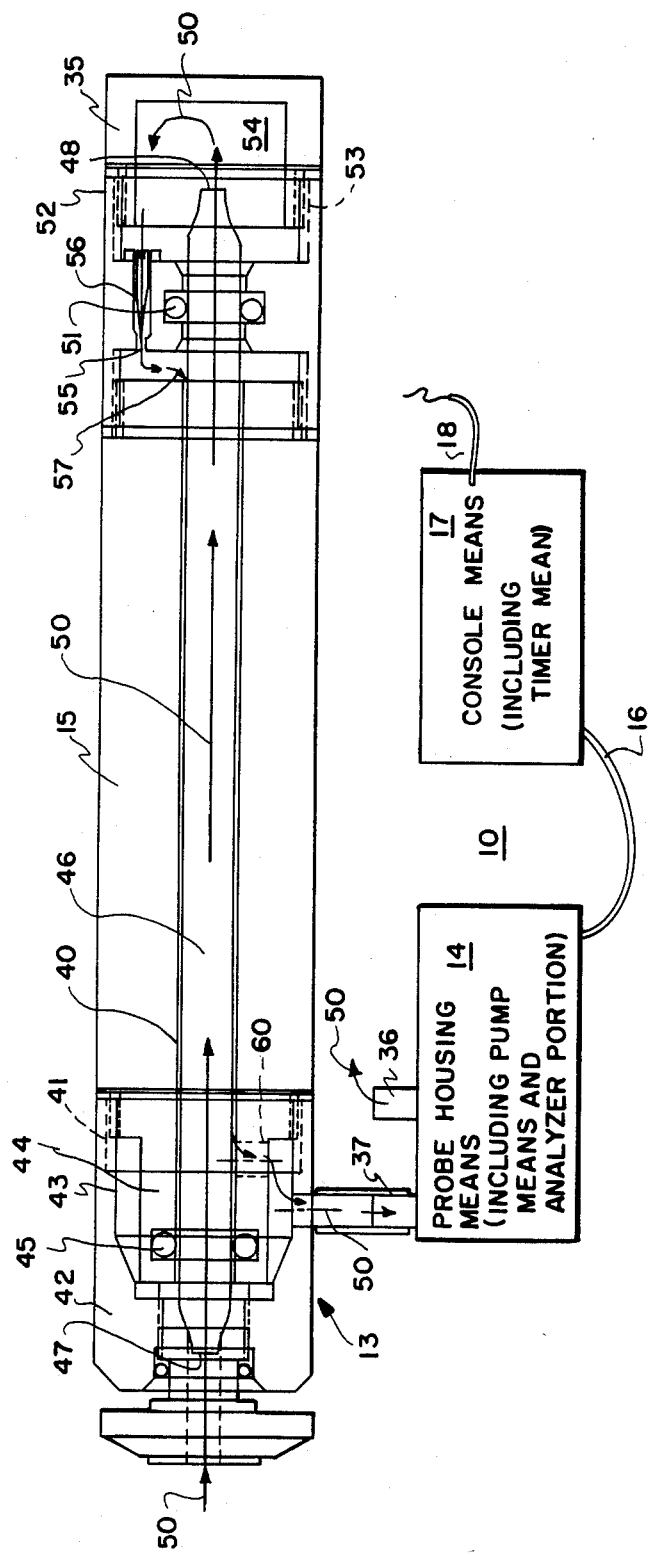
FIG. 2 is a cross-section of a cylindrical housing which is used to connect a carbon monoxide gas analyzer cell means for use.

In FIG. 2 detailed construction of the cylindrical housing means 15 is shown. Along with the details of structure, the balance of the system is schematically represented. The flue gas analyzer means is again shown at 10 having the console means 17 that is connected at 18 to a source of power and at 16 by a cable to the probe housing means 14. The probe housing means 14 is indicated as including a pump means and an analyzer portion which includes the zirconium oxide sensor. The fitting means 13 is disclosed schematically as an inlet pipe 37 to the probe housing means 14, and as the vent opening 36.

A cross-section of the cylindrical housing means 15 is disclosed attached to the fitting means 13. The cylindrical housing means 15 is a threaded tubelike member having a central bore 40 and a threaded end 41. The threaded end 41 mates with the fitting means 13. More specifically, the fitting means 13 includes a filter holder 42 with a chamber 43 that normally would contain a filter. The filter has been removed and the chamber 43 now includes a fitting 44 that has an O-ring seal 45 that seals the fitting 44 to a carbon monoxide gas analyzer cell means 46 that is shown as an elongated tube with an open end 47, and a further open end 48.

The O-ring 45 and the end 47 of the carbon monoxide gas analyzer cell means 46 is sealed so as to receive a flow of flue gas as indicated by the flow arrow 50. The flue gas enters the end 47 of the cell means 46 and travels as indicated by the arrow 50 to the end 48 of the cell means 46. The end 48 of the cell means 46 is sealed by an O-ring 51 into an end 52 of the cylindrical housing means 15. The end 52 is threaded at 53 so that the cover 35 can seal the end 52 into a reentrant flow chamber shown at 54. The reentrant flow chamber 54 allows the flow 50 to circle back and pass through an orifice 55 that is controlled by a needle valve 56. The orifice 55 and the needle valve 56 are provided for adjustment of the flow of flue gas through the device to match the pump means contained in the probe housing means 14. The needle valve 56 can be dispensed with if the orifice 56 is properly designed to match the pump.

The O-ring 51 seals the cell means 46 in a gas tight configuration so that the flue gas 50 circulates back at 57 to a space that is created between the cell means 46 and the central bore or opening 40. The flue gas flows along the means 46 until it reaches a port shown at 60 in the insert 44. The flue gas 50 then is drawn into the inlet 37 of the fitting means 13 for the probe housing means 14. The flue gas is exhausted to the atmosphere through the vent 36.

The cylindrical housing means 15 can be described as a housing member that supports the carbon monoxide gas analyzer cell means 46 in a central opening 40 so that flue gas 50 can be drawn into the end 47, through the cell means 49 46, and exhausted through the end 48 into the reentrant flow chamber 54. The flow chamber is carefully controlled by an orifice or an orifice and needle valve 55 and 56. The flue gas is then allowed to flow back within the cylindrical means 15 to the outlet or fitting means 37 to the probe housing means 14 under the action of the pump contained within the unit. As long as the pump is operated for a precise period of time, and the orifice 55 (or the orifice 55 and needle valve 56) are adjusted for the pump, a precise amount of flue gas can be sampled. This allows for a carefully controlled flow of flue gas through the cell means 46 and provides a uniform and consistent way of obtaining an accurate carbon monoxide measurement.

The present arrangement provides for a simple cylindrical housing which utilizes a single end for both the input of the flue gas and the exhaust of the flue gas thereby allowing for the convenient mounting of the cylindrical housing with the fitting means 13 to minimize the cost and size of the unit and to provide for an easy access for readout of the carbon monoxide of a flue gas sample.

The present invention has been disclosed as a very specific structure in connection with a flue gas analyzer means. The physical configuration of the structure could be altered by one skilled in the art. The limitations of the present invention are disclosed and specifically defined by the appended claims.

The embodiments of the invention in which an exclusive property or right is claimed are defined as follows:

1. A flue gas analyzer device, including: a probe adapted to be inserted in a flue gas stack to withdraw a flue gas sample for analysis; flue gas analyzer means including an analyzer portion; said analyzer means having probe housing means and console means electrically connected to form said analyzer means; said housing means including fitting means for attachment of said probe to said housing means; said housing means including pump means to draw said flue gas through said probe, said fitting means, and said analyzer portion of said flue gas analyzer means; said flue gas analyzer means also including timer means connected to said pump means to time the operation of said pump means to draw a predetermined volume of flue gas from said stack through said probe and said fitting means; and said fitting means including carbon monoxide gas analyzer cell means said pump means being in flow communication with said flue gas analyzer means so as to provide a predetermined flow of said flue gas through said carbon monoxide gas analyzer cell means at a constant rate to accurately determine the carbon monoxide content of said flue gas.

2. A flue gas analyzer device as described in claim 1 wherein said fitting means includes a cylindrical housing having a centrally located bore; said carbon monoxide gas analyzer cell means mounted in said bore in flow communication with said flue gas analyzer means so as to provide a flue gas flow path through said cell means to measure the carbon monoxide content of said flue gas upon said predetermined flow of said flue gas passing through said cell means.

3. A flue gas analyzer device as described in claim 2 wherein said cell means is mounted between a pair of O-ring seals to ensure the total flow of said flue gas is through said cell means.

4. A flue gas analyzer device as described in claim 3 wherein said cylindrical housing further includes reentrant gas flow path means and orifice means in flow communication with said pump means through which said flow of flue gas is metered by operation of said pump means to accurately control the rate of flue gas through said cell means.

5. A flue gas analyzer device as described in claim 4 wherein said reentrant gas flow path means includes a passage between said O-rings and adjacent said cell means to the atmosphere; said passage having an exit port to said pump means at said fitting means.

6. A flue gas analyzer device as described in 3 wherein said cylindrical housing further includes reentrant gas flow path means and an orifice in flow communication with said pump means and an adjustable needle valve positioned and arranged with respect to said orifice so as to adjust said flue gas flow to said pump means to ensure said accurate control of said flow of flue gas through said cell means.

7. A flue gas analyzer device as described in claim 1 wherein said fitting means includes a cylindrical housing that is constructed so as to provide a flue gas flow path and having a threaded end portion that is adapted to be removably attached to said fitting means, and including a cylindrical housing having a centrally located bore in which is mounted said carbon monoxide gas analyzer cell means; said housing providing said flue gas flow path through said cell means to measure the carbon monoxide content of said flue gas upon said predetermined flow of said flue gas passing through said cell means.

8. A flue gas analyzer device as described in claim 7 wherein said cell means is mounted between a pair of O-ring seals to ensure the total flow of said flue gas through said cell means.

9. A flue gas analyzer device as described in claim 8 wherein said cylindrical housing further includes reentrant gas flow path means and orifice means in flow communication with said pump means through which said flow of flue gas is metered by operation of said pump means to accurately control the flow of flue gas through said cell means.

10. A flue gas analyzer device as described in claim 9 wherein said reentrant gas flow path means includes a passage between said O-ring seals and adjacent said cell means to the atmosphere; said passage having an exit port to said pump means at said fitting means.

11. A flue gas analyzer device as described in claim 7 wherein said cylindrical housing further includes reentrant gas flow-path means and an orifice in flow communication with said pump means and an adjustable needle valve positioned and arranged with respect to said orifice so as to adjust said flue gas flow to said pump means to ensure said accurate control of said flow of flue gas through said cell means.

* * * * *